United States Patent
Perelman et al.

(10) Patent No.: US 12,004,989 B2
(45) Date of Patent: Jun. 11, 2024

(54) SPLINT FOR SUPPORTING AN INJURED LIMB AND/OR APPENDAGE

(71) Applicant: SPL INT, LLC, Silver Spring, MD (US)

(72) Inventors: Chava E. Perelman, Silver Spring, MD (US); Harrison B. Solomon, Bethesda, MD (US)

(73) Assignee: SPL INT, LLC, Silver Spring, MD (US)

( * ) Notice: Subject to any disclaimer, the term of this patent is extended or adjusted under 35 U.S.C. 154(b) by 130 days.

(21) Appl. No.: 17/215,671

(22) Filed: Mar. 29, 2021

(65) Prior Publication Data
US 2021/0307950 A1    Oct. 7, 2021

Related U.S. Application Data

(60) Provisional application No. 63/003,538, filed on Apr. 1, 2020.

(51) Int. Cl.
*A61F 5/058*    (2006.01)

(52) U.S. Cl.
CPC ...... *A61F 5/05825* (2013.01); *A61F 5/05875* (2013.01)

(58) Field of Classification Search
CPC .... A61F 5/05825; A61F 5/05875; A61F 5/10; A61F 5/50; A61F 5/01; A61F 5/013; A61F 5/05866; A61F 5/0118; A61F 5/04; A61F 5/0127; A61F 13/063104; A61F 13/105; A61F 2/586; A61F 2/54; A61F 2/58; A61F 2002/587; A61H 1/02
USPC ....... 602/22, 5, 12, 15, 21; 128/880; 623/59, 623/60, 62, 63, 54, 65; 482/47, 48
See application file for complete search history.

(56) References Cited

U.S. PATENT DOCUMENTS

| | | | | |
|---|---|---|---|---|
| 2,354,770 A | * | 8/1944 | Patterson | A61F 5/019 602/30 |
| 4,558,694 A | | 12/1985 | Barber | |
| 5,584,799 A | * | 12/1996 | Gray | A61F 5/05866 602/5 |
| 6,039,706 A | * | 3/2000 | Bolla | A61F 5/05866 602/5 |

(Continued)

FOREIGN PATENT DOCUMENTS

| | | |
|---|---|---|
| CN | 208876949 U | 5/2019 |
| DE | 202018000399 U1 * | 3/2018 |

(Continued)

*Primary Examiner* — Ophelia A Hawthorne
*Assistant Examiner* — Michael Milo
(74) *Attorney, Agent, or Firm* — The Webb Law Firm

(57) ABSTRACT

A splint includes a band having a first end portion, a second end portion, and a middle portion extending between the end portions. The splint also includes at least one elongated member formed from a bendable material having at least a middle portion extending axially along the middle portion of the band, a first hook portion bent relative to a longitudinal axis of the band, and a second hook portion bent relative to the longitudinal axis of the band. The splint also includes at least one first perforation positioned in the band to receive the first hook portion and a second perforation in the band positioned to receive the second hook portion for securing the end portions of the band together forming at least one loop sized to support an injured limb and/or appendage of a patient.

21 Claims, 14 Drawing Sheets

(56) References Cited

U.S. PATENT DOCUMENTS

| | | | |
|---|---|---|---|
| 2007/0021700 A1* | 1/2007 | Liebowitz | A61F 5/10 602/22 |
| 2013/0327344 A1 | 12/2013 | Zilber | |
| 2016/0270942 A1* | 9/2016 | Nakamura | A61F 5/30 |
| 2017/0079831 A1* | 3/2017 | Sayre | A61F 5/10 |
| 2017/0296371 A1* | 10/2017 | Bernardino | A61F 5/10 |
| 2022/0023084 A1* | 1/2022 | Talke | A61F 5/05866 |

FOREIGN PATENT DOCUMENTS

| | | | | |
|---|---|---|---|---|
| EP | 0020943 A1 * | 1/1981 | | F16L 3/233 |
| EP | 2671546 B1 | 10/2015 | | |
| FR | 3031897 A1 * | 7/2016 | | A61F 5/0118 |
| JP | 2006271872 A * | 10/2006 | | |
| JP | 2006271872 A | 10/2006 | | |
| JP | 2017176457 A | 10/2017 | | |

* cited by examiner

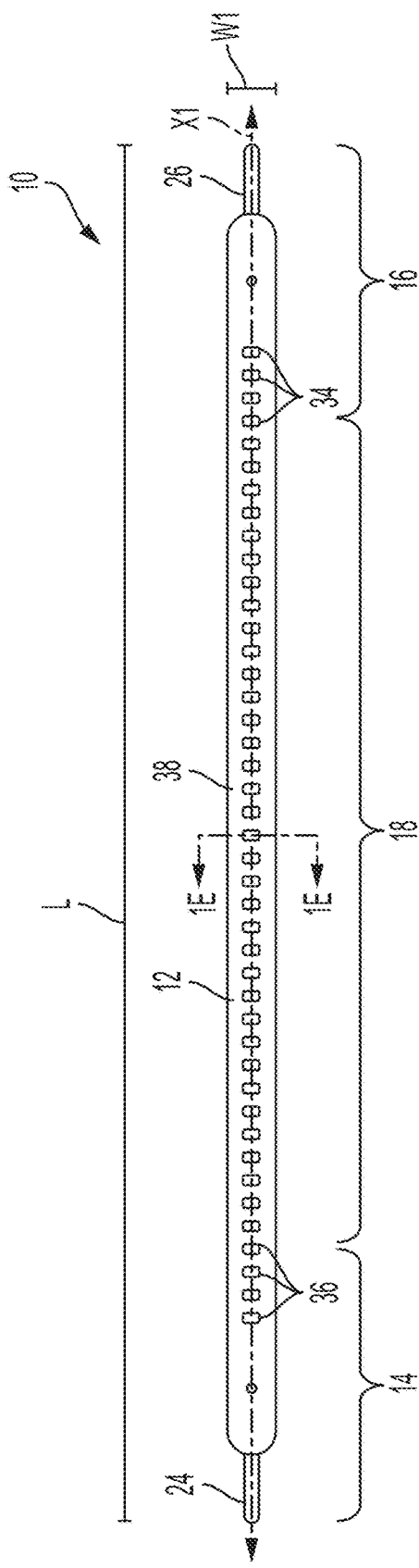
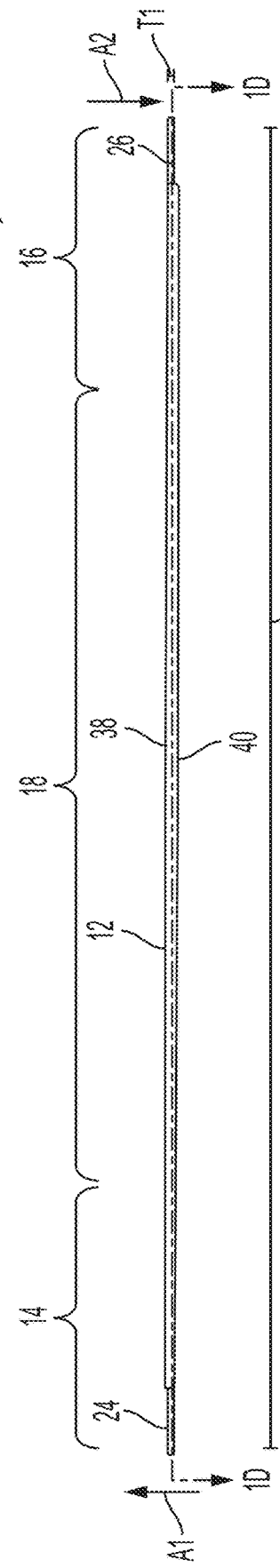

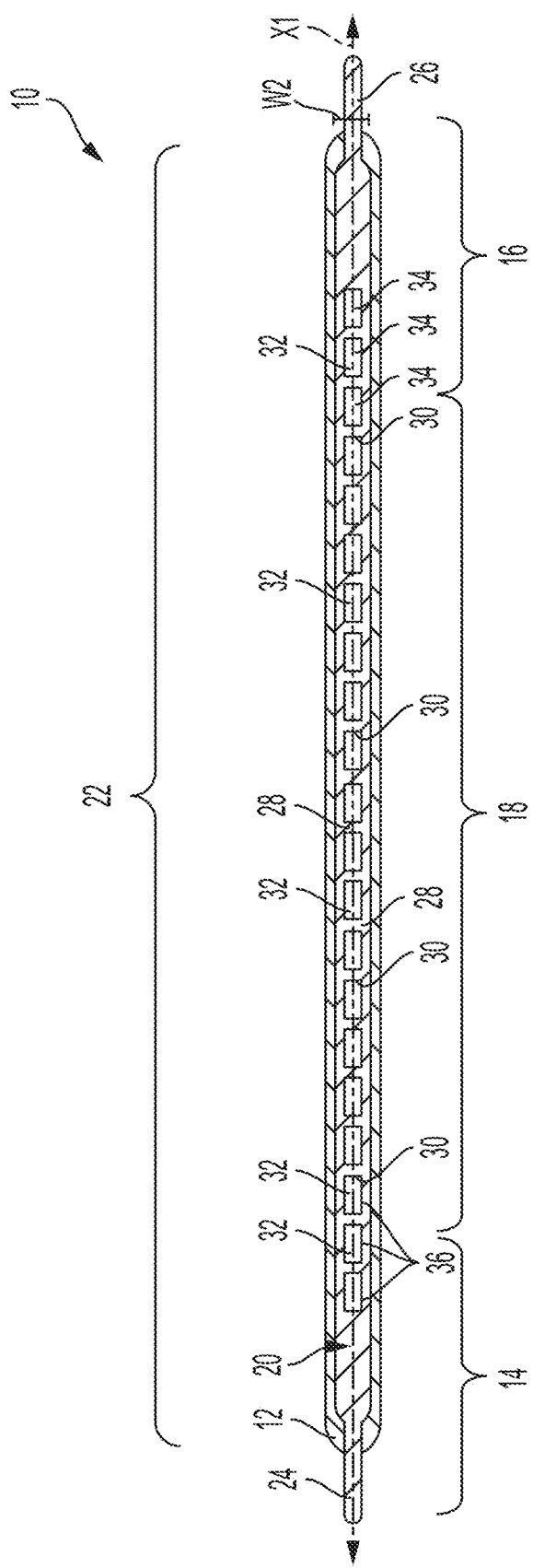
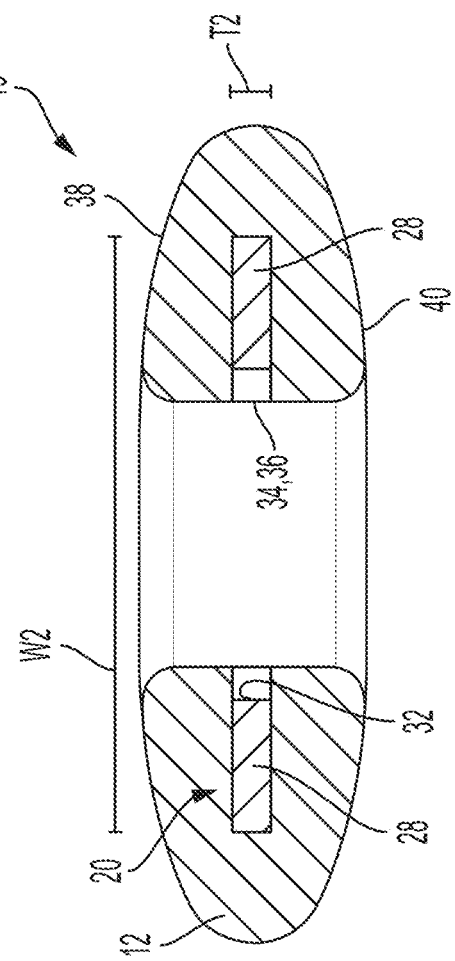
FIG. 1D
FIG. 1E

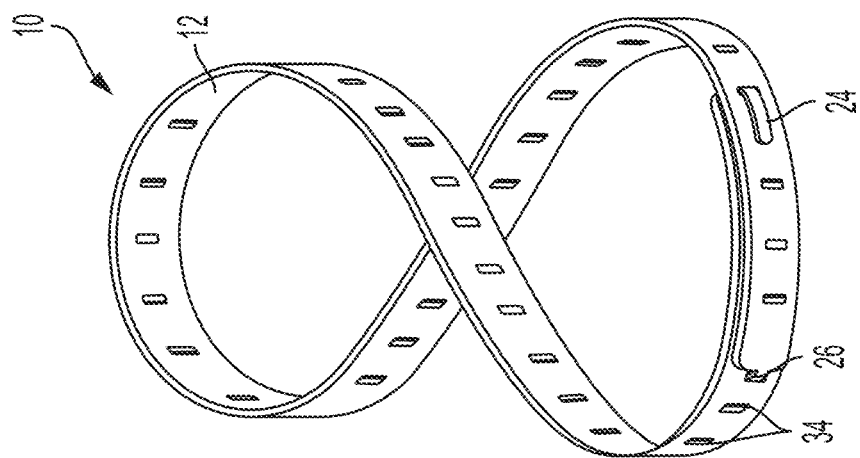
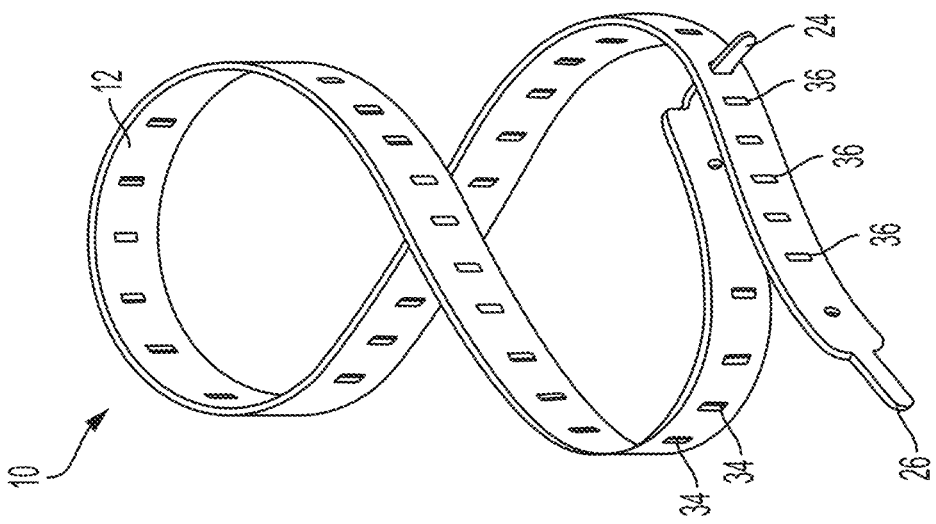

SPLINT FOR SUPPORTING AN INJURED LIMB AND/OR APPENDAGE

CROSS REFERENCE TO RELATED APPLICATION

The present application claims priority to U.S. Provisional Patent Application No. 63/003,538 entitled "Hook Splint," filed Apr. 1, 2020, the disclosure of which is hereby incorporated by reference in its entirety.

BACKGROUND OF THE INVENTION

Field of the Invention

This disclosure is directed to a splint for supporting an injured limb and/or appendage of a patient and, in particular, to a splint including an elongated bendable member at least partially connected to, embedded in, or enclosed within a band configured to be bent, molded, and/or customized to support the injured limb and/or appendage.

Description of Related Art

Splints and bandages for supporting injured appendages, such as a finger of a patient's hand, are widely available. In some cases, an injured finger may be secured against an adjacent finger using a bandage, such as a strip of fabric, tape, or an elastic band. Binding the injured finger to an adjacent finger can prevent the patient from moving the injured finger causing further injury. In other cases, rigid splints, such as flat elongated members or curved braces, may be secured to the injured finger using tape or bandages. Braces can be formed from metal or molded plastic attached to cushioning materials for comfort.

More specialized and/or custom-molded splints configured to support injured fingers and other extremities are used for particular procedures and treatments. Currently, specialized or customized splints, such as relative motion splints, are made from customized materials, such as thermoplastic(s). The customized materials must be cut down to size, heated in a warming bath, and then applied to the patient. In order to make any subsequent modifications to the customized splint (e.g., to account for swelling of injured tissues following treatment), medical personnel, such as a hand therapist, must reheat and remodel the customized splints to new sizes and shapes. More commonly, the hand therapist will discard the old splint and start with a new amount of customized material to form a new splint to the desired size and configuration.

In view of difficulties with currently available customized and/or custom-molded splints, there is a need for customizable splinting material(s) and/or devices that can be manufactured for the general population (i.e., in a limited number of sizes or configurations) and easily repeatedly customized without the complex process of reheating and/or reforming.

SUMMARY OF THE INVENTION

According to an aspect of the disclosure, a splint configured to support an injured limb and/or appendage of a patient includes a band having a first end portion, a second end portion, and a middle portion extending between the end portions and at least one elongated member formed from a bendable material at least partially enclosed by the band. The at least one elongated member includes (i) a first tab capable of being bent relative to a longitudinal axis of the middle portion of the band, (ii) a second tab capable of being bent relative to the longitudinal axis of the middle portion of the band, and (iii) a middle portion between the first tab and the second tab that extends axially through the band. The splint also includes at least one first perforation through the band sized to receive the first tab of the at least one elongated member and at least one second perforation through the band sized to receive the second tab of the at least one elongated member for securing the end portions of the band together forming at least one loop sized to wrap around at least a portion of the injured limb and/or appendage for supporting the injured limb and/or appendage.

According to another aspect of the disclosure, a method of treating an injured limb and/or appendage of a patient with a splint includes inserting a first tab of a band of the splint into at least one first perforation of the band and inserting a second tab into at least one second perforation of the band, thereby connecting end portions of the band together forming at least one loop with the first end portion of the band and a portion of at least one elongated member of the splint overlapping the second end portion of the band and another portion of the at least one elongated member to form a rigid area configured to support the injured limb and/or appendage. The method further includes, once the splint is formed into the at least one loop, sliding the splint onto the patient so that the injured limb and/or appendage rests on the splint.

According to another aspect of the disclosure, a method of making a splint includes providing at least one elongated member formed from a bendable material. The at least one elongated member includes a first tab, a second tab, and a middle portion between the first tab and the second tab. The method further includes connecting the at least one elongated member to a band having a first end portion, a second end portion, and a middle portion extending between the end portions, such that the middle portion of the at least one elongated member extends through the middle portion of the band. The method further includes forming at least one first perforation and at least one second perforation on the band, wherein the at least one first perforation is sized to receive the first tab of the at least one elongated member and the at least one second perforation is sized to receive the second tab of the at least one elongated member, thereby securing the end portions of the band together forming at least one loop sized to wrap around at least a portion of the injured limb and/or appendage for supporting the injured limb and/or appendage.

Examples of the present invention will now be described in the following numbered clauses:

Clause 1: A splint configured to support an injured limb and/or appendage of a patient, the splint comprising: a band comprising a first end portion, a second end portion, and a middle portion extending between the end portions; at least one elongated member formed from a bendable material at least partially enclosed by the band, the at least one elongated member comprising (i) a first tab capable of being bent relative to a longitudinal axis of the middle portion of the band, (ii) a second tab capable of being bent relative to the longitudinal axis of the middle portion of the band, and (iii) a middle portion between the first tab and the second tab that extends axially through the band; and at least one first perforation through the band sized to receive the first tab of the at least one elongated member and at least one second perforation through the band sized to receive the second tab of the at least one elongated member for securing the end portions of the band together forming at least one loop sized to wrap around at least a portion of the injured limb and/or appendage for supporting the injured limb and/or appendage.

Clause 2: The splint of clause 1, wherein the band comprises an elastomeric polymer, preferably polyurethane or silicone.

Clause 3: The splint of clause 1 or clause 2, wherein, when the end portions of the band are secured together forming the at least one loop, the first end portion of the band and a portion of the at least one elongated member overlap the second end portion of the band and another portion of the at least one elongated member forming a rigid area configured to support the injured limb and/or appendage.

Clause 4: The splint of any of clauses 1 to 3, wherein the at least one first perforation and the at least one second perforation comprise slots extending through the band substantially transverse to a longitudinal axis of the band.

Clause 5: The splint of any of clauses 1 to 4, comprising a plurality of the first and second perforations for adjusting a size of the loop.

Clause 6: The splint of any of clauses 1 to 5, wherein the injured limb and/or appendage comprises an injured finger.

Clause 7: The splint of clause 6, wherein the splint is configured to be wrapped around at least two adjacent fingers of the patient's hand adjacent to the injured finger and to support the injured finger of the patient's hand in flexion or extension on an outwardly facing surface of the at least one loop formed by securing the end portions of the band together around the at least two adjacent fingers.

Clause 8: The splint of any of clauses 1 to 7, wherein the first tab of the at least one elongated member is disposed at least partially within the first end portion of the band and the second tab of the at least one elongated member is disposed at least partially within the second end of the band.

Clause 9: The splint of any of clauses 1 to 8, wherein the at least one elongated member comprises a plate having a width that is greater than a thickness of the plate.

Clause 10: The splint of clause 9, wherein the middle portion of the at least one elongated member is wider than the tabs.

Clause 11: The splint of clause 9 or clause 10, wherein the middle portion of the at least one elongated member comprises at least one opening aligned with the first perforation and at least one opening aligned with the second perforation.

Clause 12: The splint of any of claims 9 to 11, wherein the middle portion of the plate comprises multiple openings, each opening aligned with two or fewer perforations of the band.

Clause 13: The splint of any of clauses 1 to 8, wherein the at least one elongated member comprises a metal wire and the band comprises an elastomeric material.

Clause 14: The splint of clause 13, wherein at least a portion of the wire is embedded in the elastomeric material of the band.

Clause 15: The splint of any of clauses 1 to 8, wherein the first tab protrudes from an upper surface of the band and the second tab protrudes from a lower surface of the band.

Clause 16: The splint of clause 15, wherein the tabs protrude from the band at about a 90 degree angle relative to the longitudinal axis of the middle portion of the band.

Clause 17: The splint of any of clauses 1 to 8 or clauses 13 to 16, wherein the at least one elongated member forms a loop comprising first and second middle portions extending axially along the middle portion of the band and the first and second tabs between the first and second middle portions.

Clause 18: The splint of clause 17, wherein the first and second middle portions of the elongated member are parallel to the longitudinal axis of the band.

Clause 19: A method of treating an injured limb and/or appendage of a patient with the splint of any of clauses 1 to 18, the method comprising: inserting the first tab of the band of the splint of any of clauses 1 to 18 into the at least one first perforation and inserting the second tab into the at least one second perforation, thereby connecting the end portions of the band together forming the at least one loop, with the first end portion of the band and a portion of the at least one elongated member overlapping the second end portion of the band and another portion of the at least one elongated member to form a rigid area configured to support the injured limb and/or appendage; and once the splint of any of clauses 1 to 18 is formed into the at least one loop, sliding the splint onto the patient so that the injured limb and/or appendage rests on the splint.

Clause 20: The method of clause 19, wherein the injured limb and/or appendage comprises an injured finger of the patient's hand, and wherein sliding the splint onto the patient comprises sliding the splint over at least two fingers of the patient's hand adjacent to the injured finger, such that the injured finger rests on an outer surface of the at least one loop and is supported by overlapped end portions of the band.

Clause 21: A method of making a splint comprising: providing at least one elongated member formed from a bendable material, the at least one elongated member comprising a first tab, a second tab, and a middle portion between the first tab and the second tab; connecting the at least one elongated member to a band comprising a first end portion, a second end portion, and a middle portion extending between the end portions, such that the middle portion of the at least one elongated member extends through the middle portion of the band; and forming at least one first perforation and at least one second perforation on the band, wherein the at least one first perforation is sized to receive the first tab of the at least one elongated member and the at least one second perforation is sized to receive the second tab of the at least one elongated member, thereby securing the end portions of the band together forming at least one loop sized to wrap around at least a portion of the injured limb and/or appendage for supporting the injured limb and/or appendage.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

BRIEF DESCRIPTION OF THE DRAWINGS

FIG. 1A is a top view of a splint, according to an aspect of the disclosure;

FIG. 1B is a side view of the splint of FIG. 1A;

FIG. 1D is a cross-sectional view of the splint of FIG. 1A taken along line 1D-1D (in FIG. 1B);

FIG. 1E is another cross-sectional view of the splint of FIG. 1A taken along line 1E-1E (in FIG. 1A);

FIG. 4A is a perspective view of the splint of FIG. 1A forming a figure-of-eight, with tabs in an unlocked position;

FIG. 4B is a perspective view of the splint of FIG. 1A forming the figure-of-eight, with the tabs in a locked position;

DETAILED DESCRIPTION OF THE PRESENT INVENTION

Figure 1C:
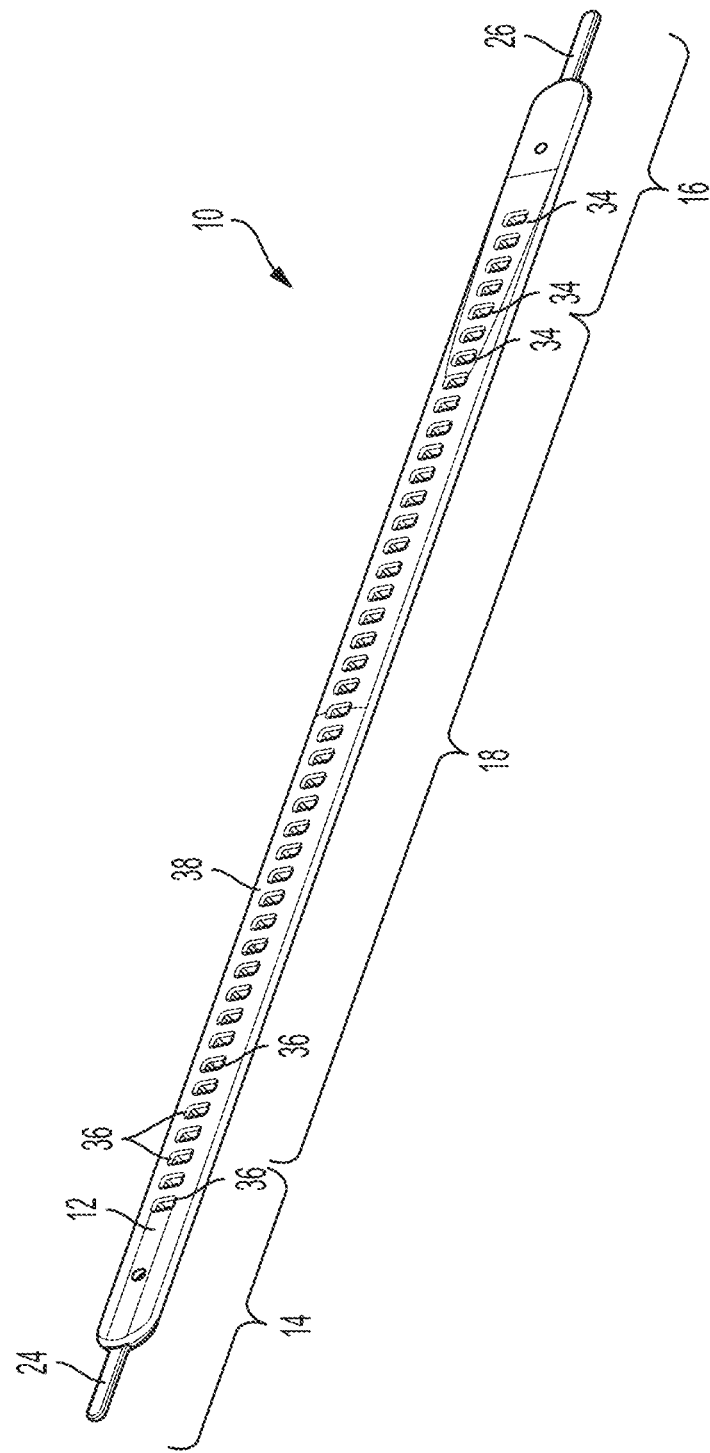
FIG. 1C is a perspective view of the splint of FIG. 1A.

For purposes of the description hereinafter, the terms "upper", "lower", "right", "left", "vertical", "horizontal", "top", "bottom", "lateral", "longitudinal," and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 2A:
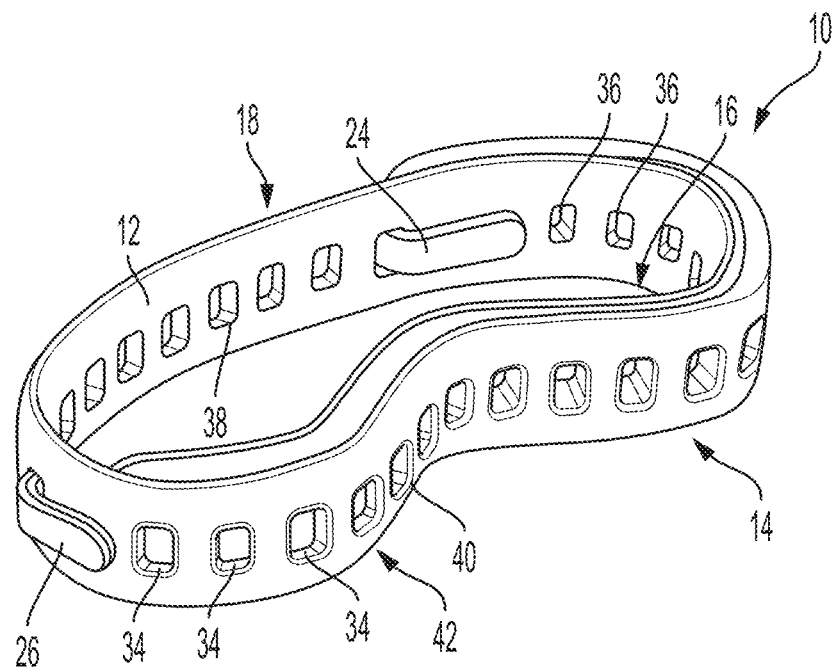
FIG. 2A is a perspective view of the splint of FIG. 1A forming a loop.
Figure 2B:
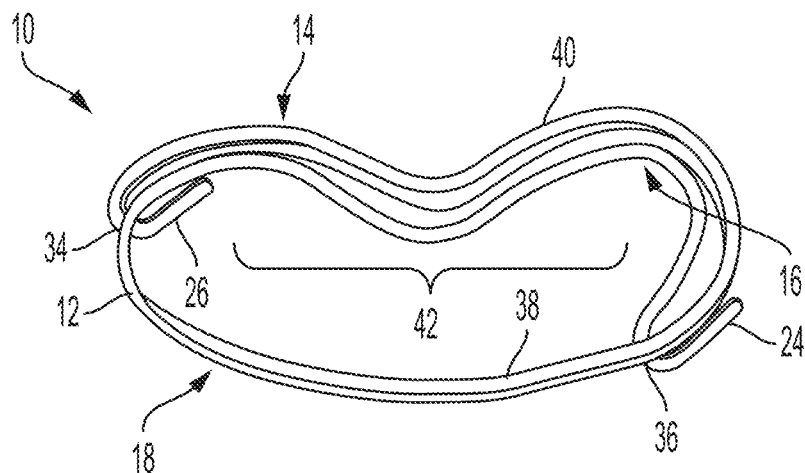
FIG. 2B is a side view of the splint of FIG. 1A forming the loop.
Figure 3A:
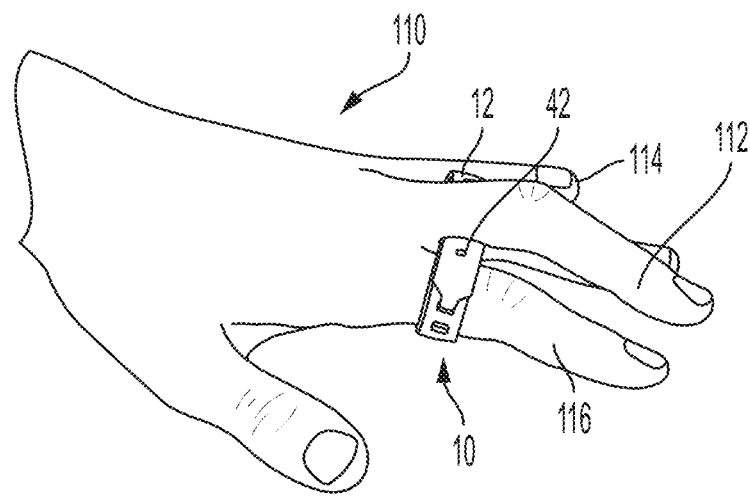
FIG. 3A is a perspective view of the splint of FIG. 1A wrapped around fingers of a patient and supporting an injured finger.
Figure 3B:
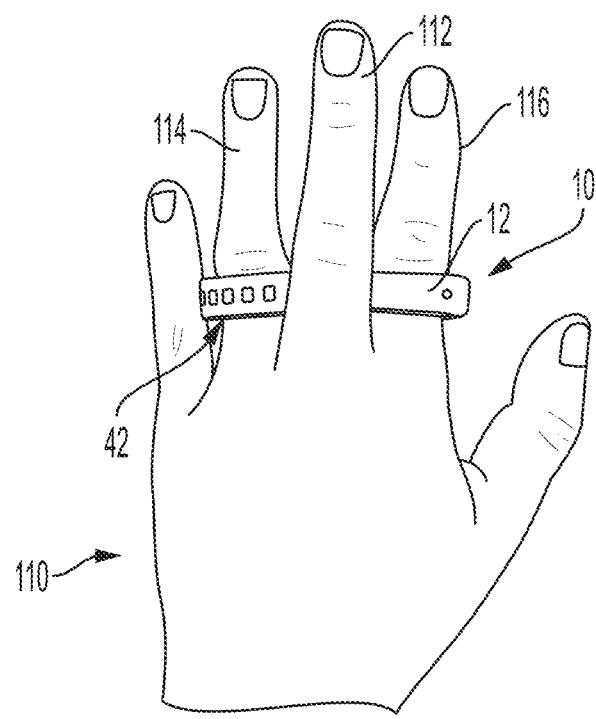
FIG. 3B is a top view of the splint of FIG. 1A wrapped around the fingers of the patient.
Figure 3C:
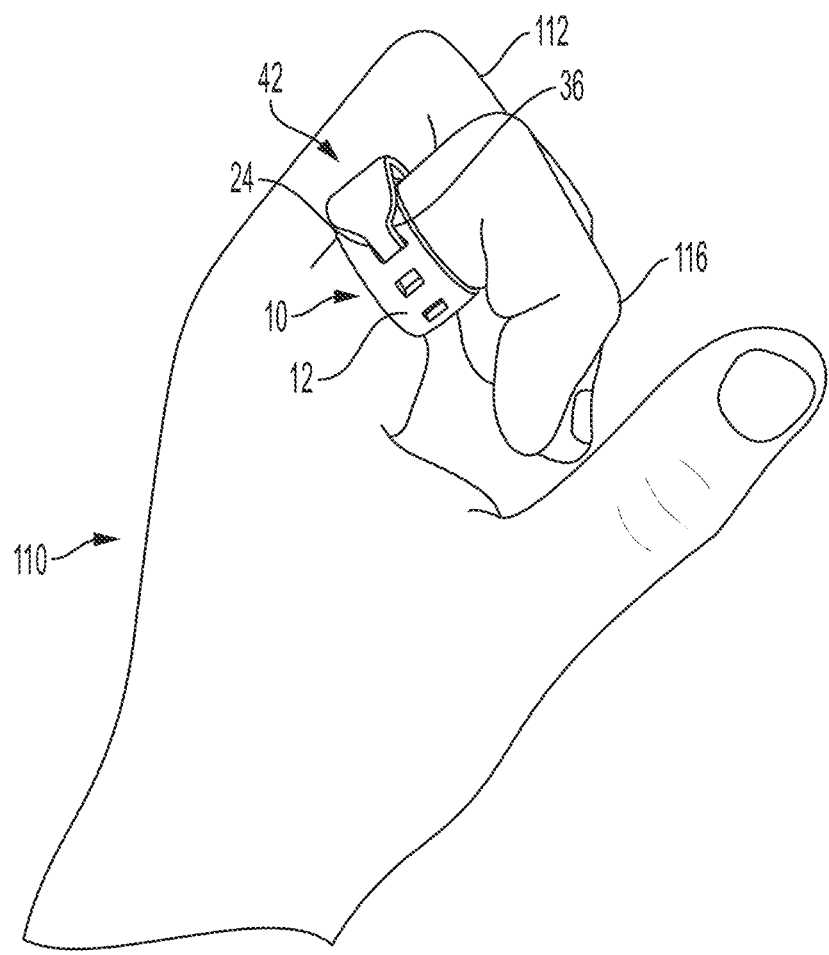
FIG. 3C is a side view of the splint of FIG. 1A wrapped around the fingers of the patient, with the injured finger in extension.
Figure 4C:
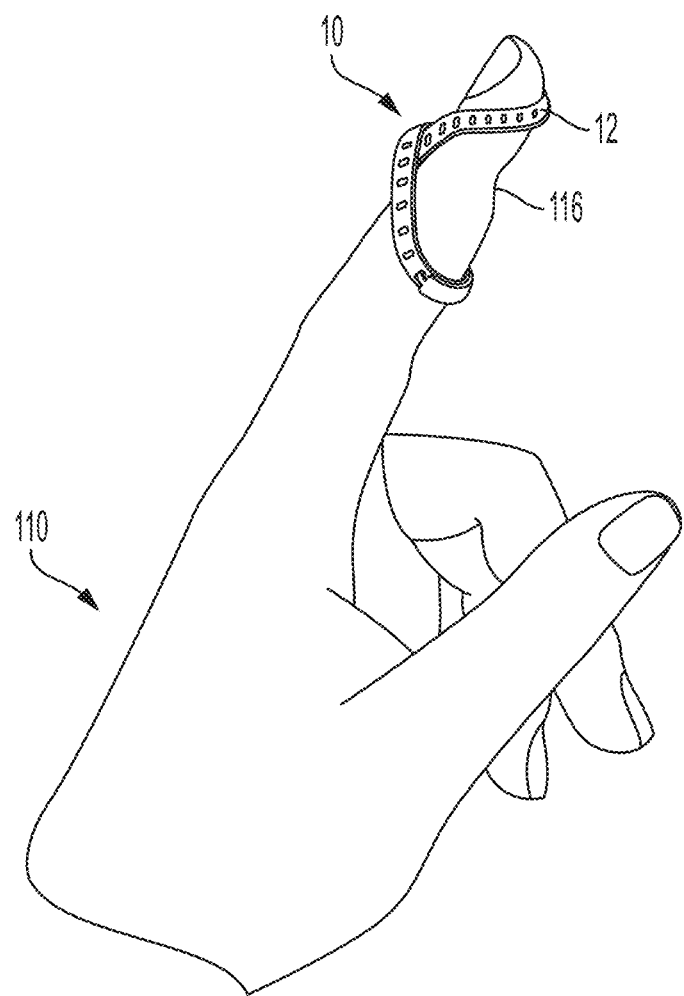
FIG. 4C is a side view of the splint of FIG. 1A wrapped around an injured finger of a patient in a figure-of-eight to support the injured finger.

With reference to FIGS. 1A-4A, and specifically FIGS. 3A-3C and 4C, a splint 10 is shown configured to support an injured limb and/or appendage of a patient. As used herein, a "limb and/or appendage" may refer, for example, to a finger, hand, wrist, arm, toes, foot, ankle, or any other body part or joint. As will be appreciated by those skilled in the art, the size (e.g., length, width, and/or thickness) of the splint 10 may be adjusted to provide appropriate support for different limbs and/or appendages. In one example, as shown in FIGS. 3A-3C and 4C, the splint 10 supports an injured finger 112, 116 of a patient's hand 110. As shown in FIGS. 3A-3C, the splint 10 can be secured to fingers 114, 116 of the patient's hand 110 on either side of the injured finger 112 (referred to herein as adjacent fingers 114, 116). For example, a patient's middle finger 112 is supported by the splint 10. The splint 10 is wrapped around the adjacent ring finger 114 and index finger 116. In FIGS. 3A-3C, the injured finger 112 is in extension in an elevated position resting on an upward facing surface of the splint 10. The splint 10 may also be used to hold the injured finger 112 in flexion, with the injured finger 112 resting below the splint 10. As shown in FIG. 4C, the splint 10 can also be wrapped around an injured index finger 116 in a figure-of-eight configuration to provide support and immobilization for an injured joint or fracture. As described herein, the splint 10 includes bendable structures or members so that the splint 10 can be custom-fit to an individual patient's hand 110 and can be adjusted to provide support for treatment of different limbs and/or appendages and for different injuries. For example, the splint 10 can be used for treating conditions including: joint contracture, boutonniere deformity, swan-neck deformity, mallet finger, trigger finger, extensor tendon laceration/repair, and/or arthritis.

As used herein, "bendable" refers to structures that are ductile and/or malleable, and which can be deformed (i.e., plastic deformation) without breaking. Once deformed, the bendable members or structures maintain a new shape or configuration and do not return to a previous shape or configuration until another deforming force is applied to the bendable structure. In particular, the bendable structures of the splint 10 should be sufficiently rigid to support the injured limb and/or appendage without deforming, bending, or otherwise changing shape or orientation.

In some examples, the splint 10 is configured to be used as a relative motion splint. As used herein, a "relative motion splint" refers to a splint configured to weave through the fingers (e.g., where a ring would sit) and which extends or flexes the injured finger 112 in an upward (shown in FIGS. 3A-3C) or downward direction "relative" to adjacent finger(s) 114, 116. This "relative" positioning can be used to treat a number of hand diagnoses. The splint 10 may also be wrapped around a finger 116 in a figure-of-eight design (as shown in FIGS. 4A-4C) for immobilization of a joint and/or fracture. In other examples, the splint 10 may be custom-fit to a thumb spica design, to support an opposable thumb. In other examples, as discussed previously, the splint 10 is used to treat conditions of other limbs and/or appendages, including the wrist, ankle, foot, or toes.

Splint with Flat Plate Support

With specific reference to FIGS. 1A-3C, and particularly FIGS. 3A-3C, the splint 10 includes a band 12 having a first end portion 14, a second end portion 16, and a middle portion 18 extending between the end portions 14, 16. The band 12 also has an upper surface 38 and a lower surface 40. The band 12 can be formed from a soft, flexible material to cushion the patient's fingers 112, 114, 116. For example, the band 12 can be formed from a soft polymeric elastomer, such as polyurethane or silicone. Desirably, the soft polymeric elastomeric material is easy to clean using, for example, soap and water, so that the splint 10 can be reused many times. In some examples, when used to provide support for injured fingers, the band 12 is an elongated structure having a length L (shown in FIGS. 1A and 1B) of about 15 cm to about 60 cm, and a width W1 (shown in FIG. 1A) of about 5 mm to about 20 mm. A thickness T1 (shown in FIG. 1B) of the band 12 may be about 1.0 mm to about 5.0 mm. The size and/or shape of the band 12 may be different for splints 10 configured to treat other limbs and/or appendages or other conditions.

The splint 10 also includes an elongated member, such as a plate 20 (shown in FIGS. 1D and 1E), formed from a bendable material and extending along and/or partially enclosed by all or at least a portion of the band 12. In other examples, the elongated member formed from the bendable material can be an elongated wire, tine, mesh, framework, or similar structural member embedded in and/or extending through the band 12. As described previously, the bendable material is adapted to deform to a new shape or configuration without breaking when a sufficient deforming force is applied. The bendable material should remain in the new shape or configuration when the deforming force is removed or ceases. The elongated member is connected to, embedded within, or at least partially enclosed by the band 12. For example, the elongated member can be fully or partially embedded in the band 12, such that the band 12 insulates the patient's fingers 112, 114, 116 from the plate 20. In some examples, the band 12 is molded around or over the elongated member, thereby permanently attaching the band 12 to the elongated member.

In some examples, the plate 20 is formed from a sheet of the bendable material. For example, the plate 20 can be formed from a flat metal sheet, such as a flat stainless steel sheet. The plate 20 can have a thickness T2 (shown in FIG. 1E) that is less than a maximum width W2 (shown in FIGS. 1D and 1E) of the plate 20. The thickness T2 is desirably selected so that the plate 20 can be easily bent, custom-fit, or adjusted to a position to support an injured limb or appendage without, for example, needing to heat the splint 10 and/or plate 20 by submerging the splint 10 in a heated water bath. The plate 20 should also be thick enough to maintain its position to support the limb or appendage resting on and/or in contact with the splint 10. For example, the thickness T2 can be about 0.5 mm to about 4.0 mm. A maximum width W2 of a middle portion 22 of the plate 20 can be about 2.0 mm to about 19.0 mm. The plate 20 can be formed by stamping or cutting a specific elongate structure from a flat sheet using manufacturing techniques known in the medical device manufacturing art.

In some examples, the plate 20 includes the middle portion 22 (shown in FIG. 1D) extending axially through the band 12 parallel to a longitudinal axial X (shown in FIGS. 1A and 1D) of the middle portion 18 of the band 12. The plate 20 also includes a first tab 24 and a second tab 26 extending axially from the middle portion 22 of the plate 20 that are capable of being bent relative to the longitudinal axis X of the middle portion 18 of the band 12 for locking ends of the splint 10 together to form one or more loops (shown in FIGS. 2A-4C).

As shown in FIGS. 1D and 1E, the middle portion 22 of the plate 20 includes axially extending portions or legs 28 on both side of the plate 20 and transverse or cross portions 30 extending between the legs 28. The legs 28 and cross portions 30 define multiple openings 32 of the plate 20 aligned in series extending axially along the plate 20. For example, as shown in FIG. 1D, the plate 20 includes twenty-three openings 32. However, the number of openings 32 is not intended to be limiting, and the plate 20 can include fewer than twenty-three or more than twenty-three openings 32 within the scope of the present disclosure.

The plate 20 also includes the tabs 24, 26 extending axially from the middle portion 22 of the plate 20. The tabs 24, 26 can be fully or partially enclosed, encapsulated, and/or embedded within the end portions 14, 16 of the band 12. Alternatively, the tabs 24, 26 can be uncovered protruding from the end portions 14, 16 of the band 12. The tabs 24, 26 are configured to be bent relative to the longitudinal axis X of the band 12 in either an upward direction (shown by arrow A1 in FIG. 1B) or downward direction (shown by arrow A2 in FIG. 1B). The tabs 24, 26 are narrower than the middle portion 22 of the plate 20, and are about the same thickness as other portions of the plate 20.

The splint 10 also includes multiple perforations 34, 36 of the band 12, referred to herein for convenience as a first perforation 34, sized to receive the first tab 24, and a second perforation 36, sized to receive the second tab 26. It is noted that not all of the perforations in the band 12 shown in FIGS. 1A-3C are identified by reference numbers 34, 36. However, any of the perforations in the band 12 can be sized to receive the first tab 24 and/or the second tab 26 for connecting end portions 14, 16 of the band 12 together and forming loops of different sizes. Further, the first perforation 34 and the second perforation 36 can be the same size and shape or may be different sizes and shapes. Also, a perforation 34, 36, such as a perforation near a middle of the band 12, may be sized and positioned to receive both the first tab 24 and the second tab 26. As shown in FIG. 1D, one or two of the perforations 34, 36 are positioned over and extend through each opening 32 in the plate 20. Inserting the tabs 24, 26 through the perforations 34, 36 secures the end portions 14, 16 of the band 12 together forming a loop (as shown in FIGS. 3A-3C) or multiple loops (as shown in FIGS. 4A-4C). As shown most clearly in FIGS. 2A and 2B, once inserted through the perforations 34, 36, the tabs 24, 26 can be bent or pressed down to lock the tabs 24, 26 in place and to prevent the tabs 24, 26 from being easily or mistakenly disconnected from the perforations 34, 36. For example, as discussed in connection with the flow chart of FIG. 6, needle nose plyers or a similar tool can be used to bend the tabs 24, 26 and to press the tabs 24, 26 into the perforations 34, 36. Further, in some examples, a tab 24, 26 can be inserted through two adjacent perforations 34, 36 to provide a more secure connection.

In some examples, the perforations 34, 36 can be slots extending through the band 12 substantially transverse to the longitudinal axis X of the band 12. In other examples, the perforations 34, 36 can have a cross-section that is circular, elliptical, rectangular, square, or any other convenient shape. In some examples, the splint 10 includes multiple perforations 34, 36 or slots positioned along the middle portion 18 and/or end portions 14, 16 of the band 12 aligned in series along the longitudinal axis X of the band 12. The slot(s) or perforations 34, 36 may be equidistantly spaced along the longitudinal axis X or can be spaced apart by varying distances. For example, perforations 34, 36 may be positioned closer together at end portions 14, 16 of the band 12 than in the middle portion 18 of the band 12. Including multiple slots or perforations 34, 36 means that the size of the loop(s) formed when the end portions 14, 16 of the band 12 are connected together may be adjustable to fit different patients with different sized fingers and hands and/or to allow for swelling, which may occur as the injured finger 112 heals. Also, the multiple slots or perforations 34, 36 in the band 12 provide for ventilation to prevent skin maceration.

The splint 10 is shown in FIGS. 2A-4C, with the end portions 14, 16 of the band 12 secured together to form one or more loops. Specifically, the first tab 24 is inserted through a first perforation 34 in the band 12 and the second tab 26 is inserted through the second perforation 36 in the band 12, thereby securing the end portions 14, 16 of the band 12 together. As shown in FIGS. 3A-3C, a loop can be sized to wrap around the two adjacent fingers (e.g., the ring finger 114 and the index finger 116) of the patient's hand 110. The patient's injured finger 112 rests on and is supported on an outwardly facing surface (e.g., the lower surface 40) of the band 12. In other examples, as shown in FIG. 4C, the splint 10 is wrapped around an injured index finger 116 in a figure-of-eight configuration to immobilize a joint and/or fracture.

As shown in FIGS. 2A-4C, when secured together, the end portions 14, 16 of the band 12 along with portions of the plate 20 at least partially overlap forming a double-walled portion or rigid zone 42. In FIGS. 3A-3C, the injured finger 112 rests on the double-walled portion or rigid zone 42 of the splint 10. The increased rigidity of the rigid zone 42 supports the weight of the injured finger 112. In particular, this double-walled portion or rigid zone 42 provides stability and rigidity for the splint 10, which allows the splint 10 to maintain its shape while supporting the injured finger 112. Other portions of the splint 10 (e.g., portions that do not support the injured finger 112) only have a single segment of the band 12 and plate 20 (e.g., single walled portion(s)), meaning that such portions of the splint 10 are less rigid, but more comfortable.

Manufacturing Method

Figure 5:
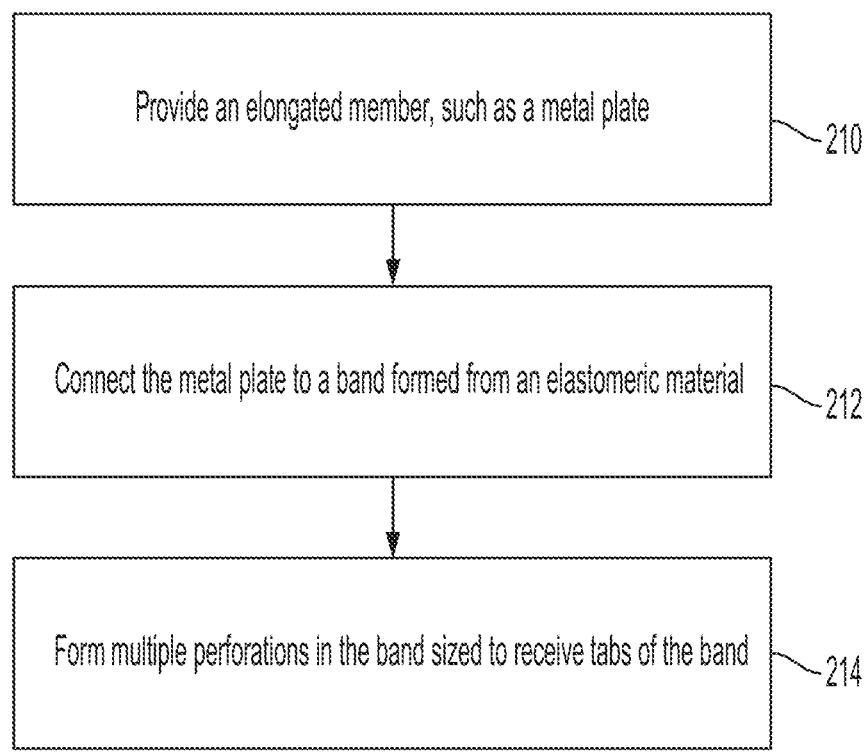
FIG. 5 is a flow chart showing a method of manufacture for a splint, according to an aspect of the disclosure.

The exemplary splints 10 disclosed herein can be made by any convenient manufacturing method, which can be determined by those skilled in the art. With reference to FIG. 5, in one example, a method for forming a splint 10 configured to support an injured limb and/or appendage of a patient includes a step 210 of providing a plate 20. As previously described, the plate 20 can be an elongated member formed from, for example, a flat sheet of metal (e.g., stainless steel). The plate 20 desirably can be easily bent for customizing the splint 10 for particular patients and/or appendages, but strong enough to maintain its shape and position to support an injury appendage once a deforming force ceases to be applied to the plate 20.

At step 212, the method further includes connecting the plate 20 to a band 12 to form the splint 10. As previously described, the band 12 comprises an elastomeric material and includes a first portion 14, second portion 16, and a middle portion 18 between the first portion 14 and the second portion 16. Once the band 12 and the plate 20 are connected together, at least a middle portion 22 of the plate 20 extends axially along the middle portion 18 of the band 12. In some examples, the band 12 is connected to the plate 20 using a conventional adhesive or bonding processes as are known in the art for manufacturing medical devices. In other examples, the band 12 is molded around all or at least a portion of the plate 20, such that the plate 20 is partially or fully encapsulated by or embedded in the band 12.

The method can further include a step 214 of forming at least one first perforation 34 and at least one second perforation 36 on the band 12. For example, once the elastomeric material of the band 12 cures and/or hardens, the perforations 34, 36 may be formed by cutting, drilling, stamping, or other conventional techniques for creating holes or openings in soft elastomeric materials. In other examples, the perforations 34, 36 can be formed during molding along with other portions of the band 12. In some examples, as shown in FIGS. 3A-3C, the first perforation 34 is sized in the band 12 to receive the first tab 24 of the plate 20 and the second perforation 36 in the band 12 is sized to receive the second tab 26 of the plate 20 for securing the end portions 14, 16 of the band 12 together forming a loop. The loop can define or include a radially inwardly facing surface (e.g., the upper surface 38 of the band 12) and a radially outwardly facing surface (e.g., the lower surface 40 of the band 12). The loop can be sized to wrap around and/or be secured to the injured limb and/or appendage of the patient to support the injured limb and/or appendage. For example, as shown in FIGS. 3A-3C, the loop can be sized to wrap around the two adjacent fingers 114, 116 and to support the injured finger 112 of the patient's hand 110 on the outwardly facing surface of the loop (e.g., the bottom surface 40 of the band 12). In other examples, the loop can be large enough to wrap around three fingers to provide added stability for supporting the injured finger 112.

Methods of Use

As discussed previously, in some examples, the splint 10 is used as a relative motion splint for supporting the injured finger 112 by positioning the injured finger 112 in extension relative to the adjacent fingers 114, 116. For example, the splint 10 can be configured to place the injured finger 112 in extension by about 30 degrees, as shown in FIGS. 3A-3C. Alternatively, the splint 10 can be flipped (i.e., with the rigid zone 42 of the splint 10 facing downward) to position the injured finger 112 in flexion. As previously discussed, the splint 10 can also be used for treating other limbs, appendages, and conditions. Other treatments and uses for the splint 10, as well as methods of preparing the splint 10 for use by different patients and/or to treat different limbs, appendages, and conditions, can be determined by those skilled in the art within the scope of the present disclosure.

Figure 6:
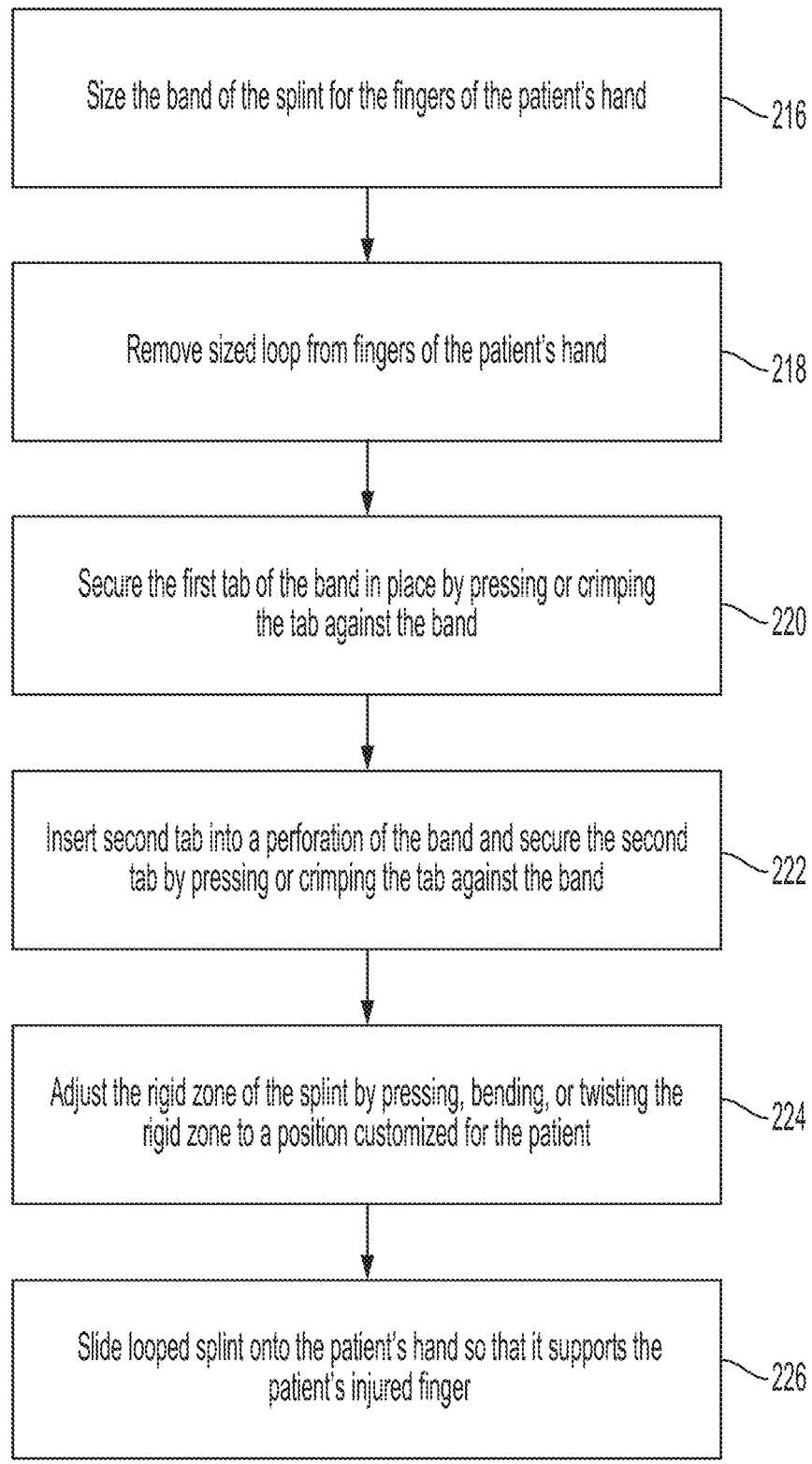
FIG. 6 is a flow chart showing a method for using a splint to support an injured finger, according to an aspect of the disclosure.

FIG. 6 is a flow chart showing a method for preparing and using the splint 10 as a relative motion splint to support the injured finger 112. The steps for preparing the splint 10 for use (i.e., sizing the splint, forming the loop, adjusting the rigid zone 42 for the patient) can be performed by a medical professional, such as a nurse, physician assistant, hand therapist, occupational therapist, physical therapist, athletic trainer, orthopedic surgeon, or similar trained medical professional. In some cases, some or all of the steps for preparing and adjusting the splint 10 can be performed by the patient. For convenience, the following method is described as being performed by a "clinician." However, it is understood that any of the above-identified individuals, as well as any other individual of similar training or experience, may perform one or more of the steps for preparing and using the splint 10.

As shown in FIG. 6, the method of treating the injured finger 112 of the patient using the splint 10 includes a step 216 of sizing the splint 10. In order to correctly size the splint 10, the clinician wraps the splint 10 around fingers 114, 116 of the patient's hand 110 adjacent to the injured finger 112, such that the injured finger 112 is not enclosed by the loop formed by the band 12. The clinician then inserts the first tab 24 into the first perforation 34 to form a loop sized for the fingers 114, 116. It is important that the loop wraps tightly around the fingers 114, 116 without much slack. When there is not much slack in the loop, the splint 10 supports the injured finger 112 in extension relative to the other fingers 114, 116 an appropriate amount. If the loop is too lose, the injured finger 112 may not be extended relative to the adjacent fingers 114, 116 by a sufficient amount to achieve desirable therapeutic results. Once the loop is formed, the clinician may ask the patient to extend and flex the fingers 112, 114, 116 to check sizing. As shown in FIGS. 3A-3C, the splint is sized for three fingers (the injured finger 112 and adjacent fingers 114, 116). Alternatively, the clinician may size the splint 10 for four fingers (the injured finger 112 and three other fingers) for added stability.

Once the required size of the loop is known, at step 218, the splint 10 is removed from the fingers 112, 114, 116. At step 220, in order to secure the first tab 24 in place, the first tab 24 can be bent into a u-shape and inserted through a perforation 34 adjacent to the first perforation 34. The tab 24 is then crimped or pressed against the band 12 to lock the first tab 24 in place so that it is not easily or mistakenly disconnected from the first perforation 34. In some examples, a tool, such as needle-nose plyers or a needle driver, may be used to assist in bending the first tab 24 and crimping it against the band 12.

At step 222 the clinician next bends the second tab 26 and inserts it into the second perforation 36. Once inserted through the perforation 36, the clinician may crimp or press the second tab 26 against the band 12 to hold it in place. The needle nose plyers or a similar tool may be used to help bend and maneuver the second tab 26. As shown in FIGS. 2A and 2B, with the tabs 24, 26 inserted into the perforations 34, 36, the end portions 14, 16 of the band 12 and portions of the plate 20 overlap forming the double-walled segment or rigid zone 42 of the splint 10.

At step 224, the clinician can press against, bend, twist, or otherwise adjust the double-walled segment or rigid zone 42 to customize or modify the rigid zone 42 to comfortably support the injured finger 112. For example, the rigid zone 42 may be pressed radially inwardly to form a depression sized to support the injured finger 112.

After the looped splint 10 is formed, at step 226, the clinician slides the splint 10 onto the patient's hand 110 to support the injured finger 112. For example, the clinician can slide the looped splint 10 over the two adjacent fingers 114, 116. The injured finger 112 is then positioned to rest on the doubled-walled segment or rigid zone 42 of the splint 10, as shown in FIGS. 3A-3C. More specifically, the injured finger 112 rests on an outer surface of the loop (e.g., the bottom surface 40 of the band 12), thereby holding the injured finger 112 in extension. As previously discussed, to place the injured finger 112 in flexion, the clinician flips the splint 10, so that the double-walled segment or rigid zone 42 faces downward. In that case, the top of the injured finger 112 rests against the doubled-walled segment or rigid zone 42.

Figure 8B:
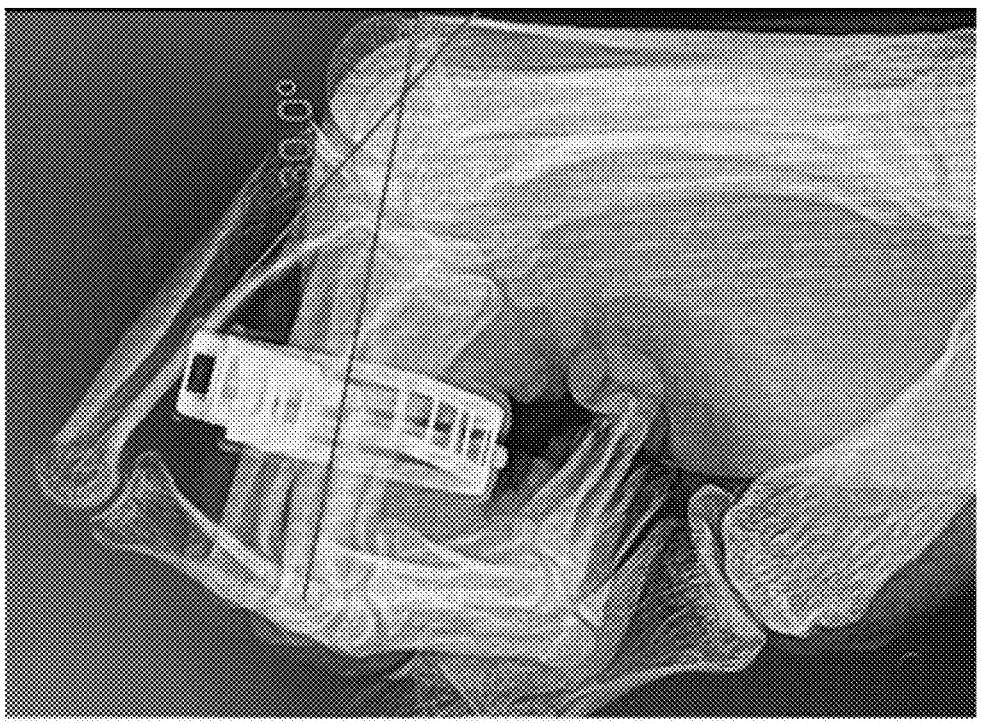
FIG. 8B is an x-ray image of the splint and injured finger shown in FIG. 8A.
Figure 8A:
FIG. 8A is a photograph of a splint of the present disclosure supporting an injured finger in extension.
Figure 9B:
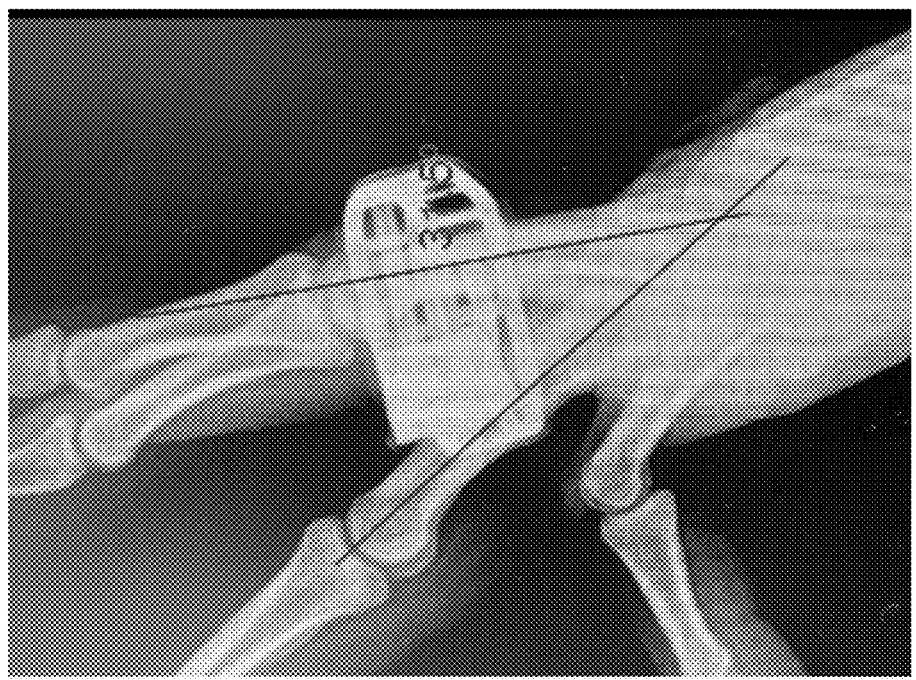
FIG. 9B is an x-ray image of the splint and injured finger shown in FIG. 9A.
Figure 9A:
FIG. 9A is a photograph of a splint of the present disclosure supporting an injured finger in flexion.

FIGS. 8A and 8B are a photograph and x-ray image showing the splint 10 used to position an injured finger 112 in extension. As shown in FIGS. 8A and 8B, the patient's injured finger (the middle finger) rests on the splint elevated relative to the adjacent fingers (the ring and index fingers). As shown in FIG. 8B, the splint 10 holds the injured finger 112 in extension by 30 degrees. FIGS. 9A and 9B are a photograph and an x-ray image showing the injured finger 112 in flexion. As shown in FIGS. 9A and 9B, the injured finger (the middle finger) rests against the bottom of the splint below the adjacent fingers. As shown in FIG. 9B, the injured finger is in flexion by 31.5 degrees in a downward direction relative to the adjacent ring finger and index finger.

Splint with Wire Support

Figure 7A:
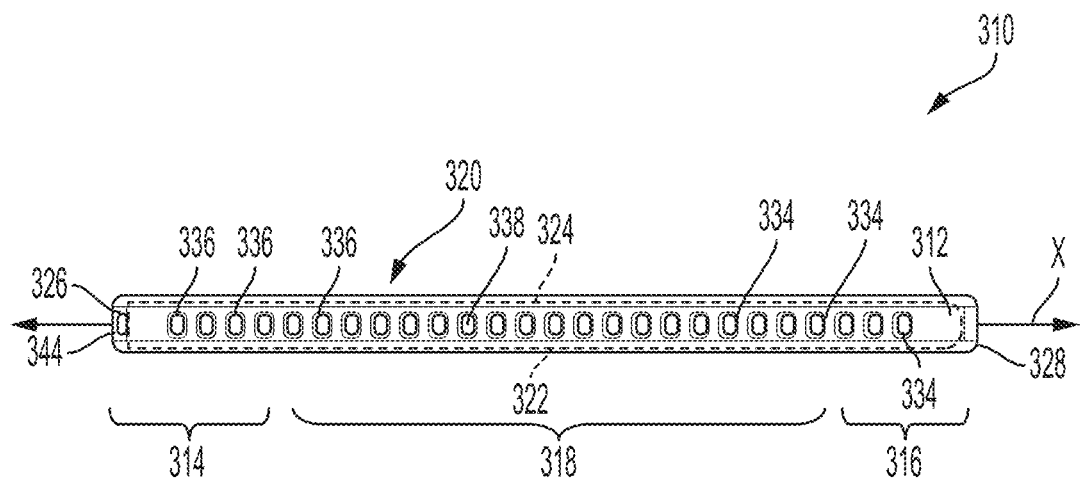
FIG. 7A is a top view of another example of a splint, according to an aspect of the disclosure.
Figure 7B:
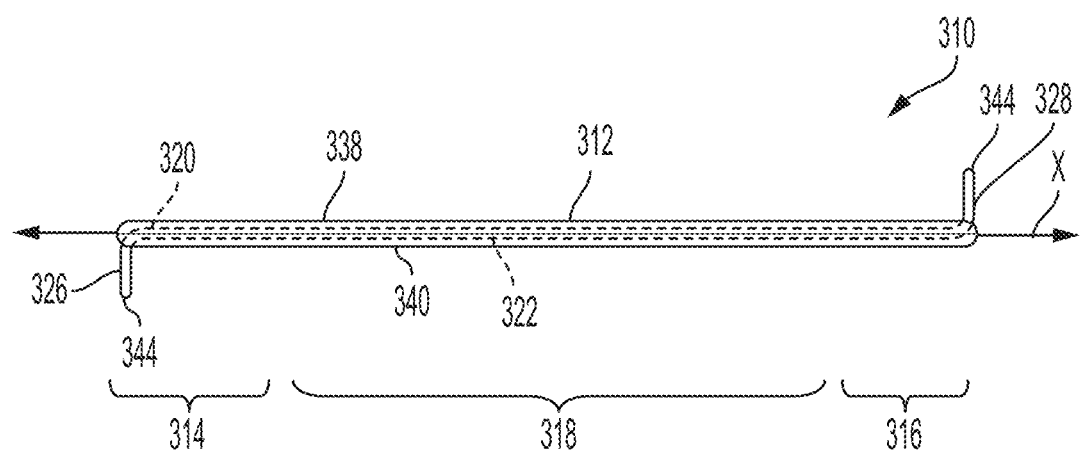
FIG. 7B is a side view of the splint of FIG. 7A.
Figure 7C:
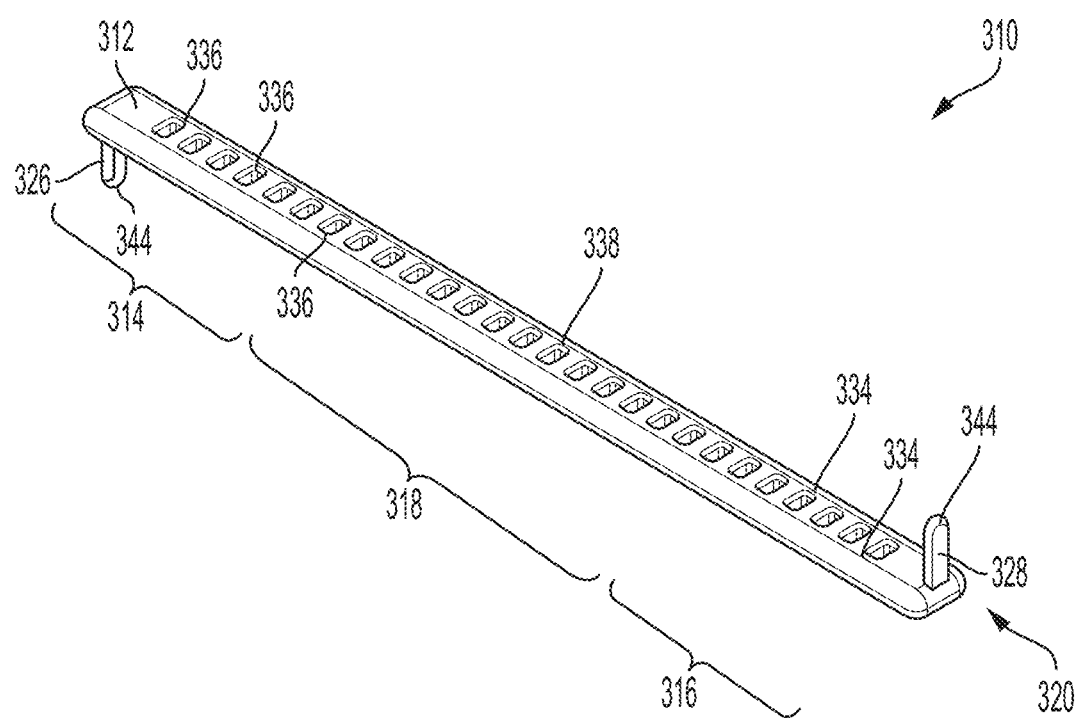
FIG. 7C is a perspective of the splint of FIG. 7A.

FIGS. 7A to 7C show another example of a splint 310 configured to support an injured limb and/or appendage of a patient. As in previous examples, the splint 310 includes a band 312 having a first end portion 314, a second end portion 316, and a middle portion 318 between the end portions 314, 316. The splint 310 also includes the multiple perforations 334, 336 aligned in series along a longitudinal axis X (shown in FIGS. 7A and 7B) of the band 312. As in previous examples, the perforations 334, 336 can be slots extending transverse to the longitudinal axis X of the band 312 or any other convenient shape, such as circular, elliptical, rectangular, square, or others.

The splint 310 also includes an elongated member formed from a bendable material connected to, embedded in, or at least partially enclosed by the band 12. However, unlike in previous examples, the elongated member of the splint 310 is a bendable wire 320 bent to form a continuous loop. The wire 320 can be formed from metal, such as stainless steel, and is sized to bend easily (without being heated), and which maintains its position once a deforming force ceases so that the splint 310 supports the injured limb or appendage.

In some examples, the looped wire 320 includes middle segments or portion(s) 322, 324 (shown by dashed lines in FIGS. 7A and 7B) extending parallel to a longitudinal axial X (shown in FIGS. 7A and 7B) of the band 312 on either side of the perforations 334, 336. The wire 320 also includes or forms a first tab 326 bent relative to the longitudinal axis X of the band 312 and a second tab 328 bent relative to the longitudinal axis X. As shown in FIGS. 7A to 7C, the tabs 326, 328 extend through portions of an upper surface 338 or a lower surface 340 of the band 312 forming hooks at bent portions 344 of the wire 320. The first tab 326 can be positioned near or extend from the first end portion 314 of the band 312 and the second tab 328 can be positioned near or extend from the second end portion 316 of the band 312. In some examples, the tabs 326, 328 may extend in opposite directions. For example, the first tab 326 extends or protrudes from the lower surface 340 of the band 312 and the second tab 328 extends or protrude from the upper surface 338 of the band 312. In other examples, both tabs 326, 238 can extend from the same surface 338, 340 of the band in the same direction. The tabs 326, 328 may protrude from the band 312 at any angle, such as about 90 degrees relative to the longitudinal axis X of the band 312.

As in previous examples, the tabs 326, 328 are sized and configured to be inserted into the first perforation 334 and the second perforation 336, respectively, for securing end portions 314, 316 of the band 312 together forming a loop or loops sized to wrap around at least a portion of the injured limb and/or appendage for supporting the injured limb and/or appendage. As in previous examples, when the splint 310 is formed into a loop, there is an overlapping or rigid zone (not shown in FIGS. 7A to 7C) formed where end portions 314, 316 of the band 312 and portions of the wire 320 overlap. As previously discussed, this overlapping or rigid zone (also referred to herein as a double-walled portion) is intended to provide substantial support for the injured appendage or limb. Other portions of the looped splint 310 (i.e., portions of the splint 310 not intended to support the injured appendage or limb) are single-walled portions, which are less rigid, but more comfortable, than the double-walled portions. For example, the splint 310 can be formed into a loop to support an injured finger in the same manner as the splint 10 in FIGS. 3A-3C. The splint 310 can also be formed into a figure-of-out loop in the same manner as the splint 10 shown in FIGS. 4A-4C.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. Furthermore, it is to be understood that the present invention contemplates that, to the extent possible, one or more features of any embodiment can be combined with one or more features of any other embodiment.

The invention claimed is:

1. A splint configured to support an injured digit of a patient, the splint comprising:
   a band comprising a first end portion, a second end portion, and a middle portion extending between the first end portion and the second end portion of the band;
   at least one elongated member formed from a bendable material at least partially enclosed by the band, the at least one elongated member comprising (i) a first tab on a first latitudinal end of the at least one elongated member capable of being bent along a bending line transverse to a longitudinal axis of the middle portion of the band, (ii) a second tab on a second latitudinal end of the at least one elongated member capable of being bent along a bending line transverse to the longitudinal axis of the middle portion of the band, and (iii) a middle portion between the first tab and the second tab that extends axially through the band; and
   at least one first perforation through the band sized to receive the first tab of the at least one elongated member and at least one second perforation through the band sized to receive the second tab of the at least one elongated member for securing the first end portion and the second end portion of the band together, thereby providing the splint in a loop configuration sized to wrap around at least a portion of the injured digit,
   wherein, in the loop configuration, the first end portion and the second end portion of the band form an overlapping region for supporting the injured digit in which the first and second end portions are fixed together by the first tab inserted into the at least one first perforation and the second tab inserted into the at least one second perforation, and wherein, in the loop configuration, the splint is configured to be wrapped around at least two supporting digits, which are adjacent to the injured digit, and to support the injured digit on an outwardly facing surface of the overlapping region, with the injured digit moved vertically downward during flexion of a proximal interphalangeal joint, and with the injured digit moved vertically upward during extension of the proximal interphalangeal joint.

2. A method of treating an injured digit of a patient with the splint of claim 1, the method comprising:
   inserting the first tab of the band of the splint of claim 1 into the at least one first perforation and inserting the second tab into the at least one second perforation, thereby connecting the first end portion and the second end portion of the band together such that the splint is in the loop configuration, with the first end portion of the band and a portion of the at least one elongated member overlapping the second end portion of the band and another portion of the at least one elongated member forming the overlapping region configured to support the injured digit;
   once the splint of claim 1 is in the loop configuration, sliding the splint onto the at least two supporting digits of the patient; and
   positioning the injured digit so that the injured digit rests against the outwardly facing surface of the overlapping region of the band, with the band supporting the injured digit in flexion, with the injured digit moved vertically downward, or in extension, with the injured digit moved vertically upward.

3. The method of claim 2, wherein the splint is positioned on the hand of the patient and the overlapping region extends from a dorsal surface of one of the uninjured fingers, to a volar surface of the injured finger, and to a dorsal surface of the other of the uninjured fingers.

4. The method of claim 2, further comprising pressing against the overlapping region of the band causing the at least one elongated member to bend providing a customized fit for comfortably supporting the injured digit.

5. The method of claim 2, wherein the injured digit is positioned against the outwardly facing surface of the overlapping region, with a longitudinal axis of the injured digit being at a longitudinal height that is greater than longitudinal heights of longitudinal axes of the at least two supporting digits with the injured digit in both flexion and extension.

6. The method of claim 2, wherein the injured digit is positioned against the outwardly facing surface of the overlapping region in flexion, with the injured digit moved vertically downward from an unbiased, natural position to a lowered, biased position, or extension, with the injured digit moved vertically upward from the unbiased, natural position to an elevated biased position.

7. The splint of claim 1, wherein the first tab protrudes from an upper surface of the band and the second tab protrudes from a lower surface of the band.

8. The splint of claim 7, wherein the first tab and the second tab protrude from the band at about a 90 degree angle relative to the longitudinal axis of the middle portion of the band.

9. The splint of claim 1, wherein the band comprises polyurethane or silicone.

10. The splint of claim 1, wherein the overlapping region is a rigid area configured to support the injured digit.

11. The splint of claim 1, wherein the at least one first perforation and the at least one second perforation comprise slots extending through the band transverse to a longitudinal axis of the band.

12. The splint of claim 1, comprising a plurality of the first and second perforations for adjusting a size of the loop.

13. The splint of claim 1, wherein the first tab of the at least one elongated member is disposed at least partially within the first end portion of the band and the second tab of the at least one elongated member is disposed at least partially within the second end portion of the band.

14. The splint of claim 1, wherein the at least one elongated member comprises a plate having a width that is greater than a thickness of the plate, the plate comprising multiple openings, each opening aligned with two or fewer perforations of the band, and
   wherein the middle portion of the at least one elongated member comprises at least one opening aligned with the at least one first perforation of the band and at least one opening aligned with the at least one second perforation of the band.

15. The splint of claim 1, wherein the at least one elongated member comprises a metal wire and the band comprises an elastomeric material, wherein at least a portion of the wire is embedded in the elastomeric material of the band.

16. The splint of claim 1, wherein the at least one elongated member forms a loop partially embedded within the band comprising first and second middle portions extending axially along the middle portion of the band and the first and second tabs between the first and second middle portions.

17. The splint of claim 1, wherein the splint is in the loop configuration and the overlapping region is configured to be of sufficient length to contact a dorsal surface of a first finger of a hand of the patient, a volar surface of a second finger of the hand adjacent to the first finger, and a dorsal surface of a third finger of the hand adjacent to the second finger.

18. The splint of claim 1, wherein the splint is configured to be wrapped around the at least two supporting digits and to support the injured digit on the outwardly facing surface of the overlapping region, with a longitudinal axis of the injured digit being at a longitudinal height that is greater than longitudinal heights of longitudinal axes of the at least two supporting digits in both flexion and extension.

19. The splint of claim 1, wherein the splint is configured to support the injured digit on the outwardly facing surface of the overlapping region in flexion, with the injured digit moved vertically downward from an unbiased, natural position to a lowered biased position, or extension, with the injured digit moved vertically upward from the unbiased, natural position to an elevated biased position.

20. The splint of claim 1, wherein the splint is configured to be wrapped around proximal phalanges of the at least two supporting digits and to support a proximal phalanx of the injured digit.

21. The splint of claim 1, wherein sliding the splint onto the at least two supporting digits of the patient comprises sliding the splint onto proximal phalanges of the at least two supporting digits, such that the splint is wrapped around the proximal phalanges of the at least two supporting digits, and
   wherein positioning the injured digit comprises resting a proximal phalanx of the injured digit against the outwardly facing surface of the overlapping region of the band.

* * * * *